United States Patent [19]

Varma

[11] 4,133,811
[45] Jan. 9, 1979

[54] 13-ALKYLTHIO (AND ARYLTHIO)-11,17-EPOXY-17-METHYL-18-NORANDROSTENES

[75] Inventor: Ravi K. Varma, Belle Mead, N.J.

[73] Assignee: E. R. Squibb & Sons, Inc., Princeton, N.J.

[21] Appl. No.: 879,015

[22] Filed: Feb. 17, 1978

[51] Int. Cl.² .................... C07J 17/00; C07J 31/00
[52] U.S. Cl. .................... 260/239.55 R; 260/397.45; 424/241
[58] Field of Search /Machine Searched Steroids

[56] References Cited
U.S. PATENT DOCUMENTS 4,081,538  3/1978  Ulick ........................... 424/241

*Primary Examiner*—Ethel G. Love
*Attorney, Agent, or Firm*—Lawrence S. Levinson; Merle J. Smith; Donald J. Barrack

[57] ABSTRACT

Steroids having the formula

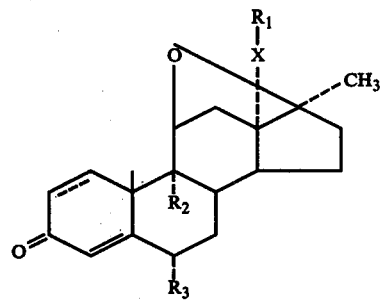

wherein X is —S—,

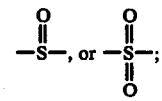

$R_1$ is alkyl or aryl; $R_2$ is hydrogen or halogen; and $R_3$ is hydrogen, fluorine or methyl; can be used as antiinflammatory agents.

17 Claims, No Drawings

13-ALKYLTHIO (AND ARYLTHIO)-11,17-EPOXY-17-METHYL-18-NORANDROSTENES

SUMMARY OF THE INVENTION

Steroids having the formula

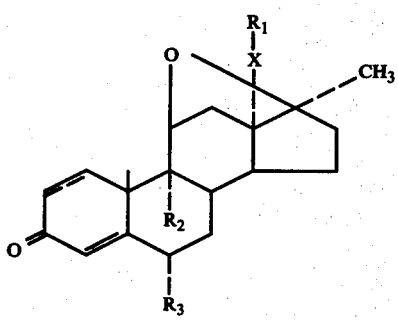

can be used as antiinflammatory agents. In formula I, and throughout the specification, the symbols are as defined below. X is —S—,

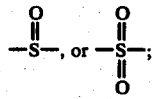

$R_1$ is alkyl, phenyl or phenyl substituted with one or two alkyl, alkoxy or halogen substituents;
$R_2$ is hydrogen or halogen; and
$R_3$ is hydrogen, fluorine or methyl.

The terms "alkyl" and "alkoxy", as used throughout the specification, refer to groups having 1 to 10 carbon atoms.

The term "halogen", as used throughout the specification, refers to fluorine, chlorine, bromine and iodine.

DETAILED DESCRIPTION OF THE INVENTION

The steroids of this invention can be prepared utilizing as starting materials androstenes having the formula

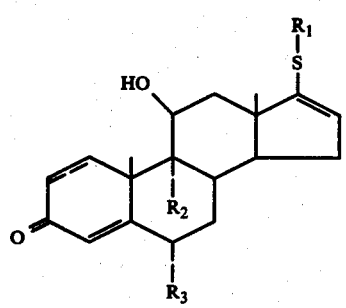

The androstenes of formula II are prepared according to the procedure disclosed in copending United States patent application Nos. 796,292, filed May 12, 1977, now U.S. Pat. No. 4,091,036 and 796,293, filed May 12, 1977, now U.S. Pat. No. 4,094,840. As disclosed therein an androstene having the formula

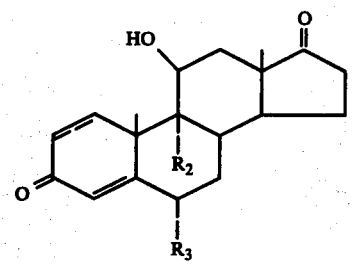

can be reacted with a thiol compound having the formula

IV 1. $R_1$-SH in the presence of a Lewis acid (e.g., boron trifluoride etherate) to yield a steroid having the formula

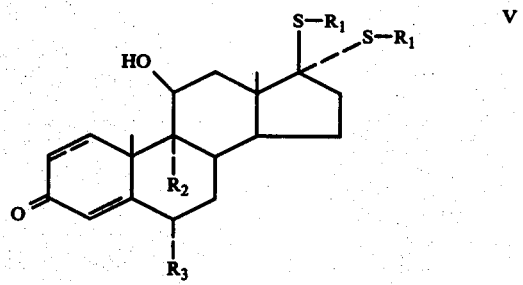

The reaction can be run in an organic solvent (e.g., a halogenated hydrocarbon) or mixture of organic solvents. The use of some glacial acetic acid improves yields. Reaction conditions are not critical, and the reaction can be conveniently run at room temperature, preferably in an inert atmosphere (e.g., argon or nitrogen). Better yields may be obtained with relatively short reaction times (less than 1 hour).

An androstene of formula V can be converted to the corresponding steroid of formula II by simply heating the steroid in an inert solvent (e.g., diethylbenzene or dichlorobenzene).

A steroid of formula II will rearrange to yield the corresponding steroid product of formula I having the formula

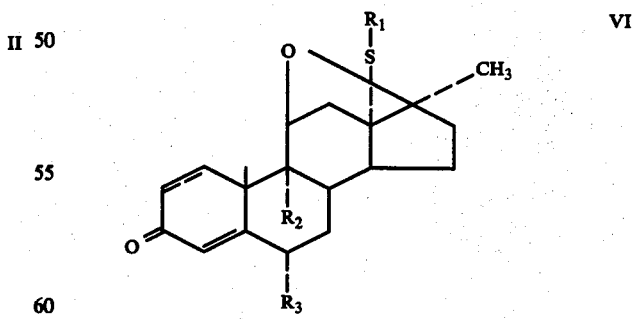

when exposed to a Lewis acid in a nonprotic solvent. Exemplary Lewis acids are boron trifluoride etherate (which is the preferred Lewis acid), stannic chloride, zinc chloride, and aluminum chloride.

Oxidation of an androstene of formula VI with a peracid (e.g., m-chloroperbenzoic acid), a peracid salt (e.g., sodium-m-periodate) or a peroxide (e.g., hydrogen peroxide) yields the corresponding sulfinyl steroid having the formula

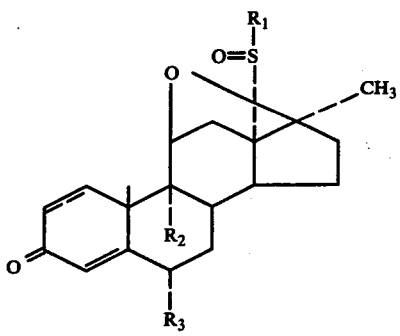

or the corresponding sulfonyl steroid having the formula

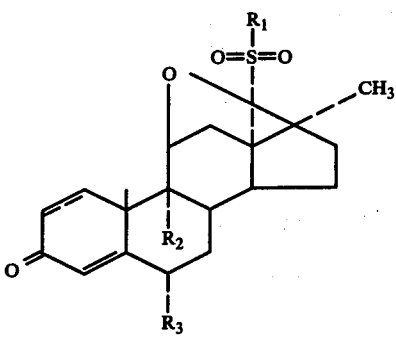

The use of one equivalent of oxidizing agent will yield predominantly the sulfinyl steroid of formula VII and the use of two or more equivalents of oxidizing agent will yield predominantly the sulfonyl steroid of formula VIII. Meta-chloroperbenzoic acid is the preferred oxidizing agent. The oxidation reaction can be run in an organic solvent, e.g., a halogenated hydrocarbon such as chloroform. Alternatively, the sulfonyl steroid of formula VIII can be prepared by oxidizing the corresponding sulfinyl steroid of formula VII.

Those steroids of formula I wherein X is

i.e., the sulfinyl steroids, exist as a mixture of stereoisomers because of asymmetry at the sulfur atom. These isomers are separable by conventional chromatography procedures.

The steroids of formula I can be used in lieu of known glucocorticoids in the treatment of inflammatory conditions; e.g., rheumatoid arthritis. They can be administered in the same manner as hydrocortisone, the dosage being adjusted for the relative potency of the particular steroid. Additionally, the steroids of this invention can be used topically in lieu of known glucocorticoids in the treatment of skin conditions such as dermatitis, psoriasis, sunburn, neurodermatitis, eczema or anogenital pruritus.

When given orally, the steroids of this invention may be used in a dosage range of 0.1 to 200 milligrams, preferably 0.3 to 100 milligrams, for a 70 kg. mammal. If administered topically, the steroids of this invention may be used in the range of 0.01 to 5.0% by weight, preferably 0.05 to 2.0% by weight, in a conventional cream, ointment, lotion or the like.

The following examples are specific embodiments of this invention.

EXAMPLE 1

(11$\beta$, 13$\alpha$,17$\beta$)-11,17-Epoxy-9-fluoro-17-methyl-13-(methylthio)-18-norandrosta-1,4-dien-3-one (A)

9-Fluoro-11$\beta$-hydroxy-17,17-bis(methylthio)androsta1,4-dien-3-one

A solution of 9-fluoro-11$\beta$-hydroxyandrosta-1,4-diene3,17-dione (8.0 g) in glacial acetic acid (70 ml) is mixed at room temperature with a solution of methanethiol (12 g) in dichloromethane (70 ml) and boron trifluoride etherate (2.5 ml). After 1.0 hour, the mixture is poured into water and diluted with chloroform. The organic layer is then separated, washed with a dilute sodium bicarbonate solution and water, dried and evaporated in vacuo. The residue is absorbed on a column of silica gel (100 g). Elution of the column with chloroform removed the nonsteroidal impurities and a product resulting from thiol addition to $\Delta^1$. Subsequent elution with chloroform affords the desired material as a solid (3.9 g). Finally, elution with chloroform-ethyl acetate (95:5) affords the unreacted steroid (345 mg). A specimen of the 3.9 g solid is crystallized once from chloroform-methanol to afford the analytical sample of the title compound, melting point 305° C. (dec.).

(B)

9-Fluoro-11$\beta$-hydroxy-17-(methylthio)androsta-1,4,16-trien-3-one

A suspension of 9-fluoro-11$\beta$-hydroxy-17,17-bis(methylthio)androsta-1,4-diene-3-one (3.6 g) in diethylbenzene (250 ml) is slowly distilled from a bath at 220° C. In a few minutes, a clear solution results and the starting material disappears. On cooling in an ice bath, the solution deposits small needles of the analytical specimen of the title compound, (2.9 g), melting point 268° C. (dec.). (discoloration starts at 263° C.).

(11$\beta$,13$\alpha$, 17$\beta$)-11,17-Epoxy-9-fluoro-17-methyl-13-(methylthio)-18-norandrosta-1,4-dien-3-one To a stirred suspension of 9-fluoro-11$\beta$-hydroxy-17-(methylthio)androsta-1,4,16-triene-3-one (696 mg) in dry dicloromethane (150 ml) is added freshly distilled boron trifluoride etherate (0.5 ml). The steroid dissolves. After 2.0 hours, the reaction is quenched by the addition of an excess of saturated sodium bicarbonate solution, the dichloromethane layer is separated, washed with water, dried and evaporated to a residue. This is subjected to preparative thin-layer chromatography on silica gel plates (using chloroform-methanol, 97:3) for development to afford 310 mg of the title compound, melting point 148°–149° C. after crystallization from acetone-hexane.

EXAMPLE 2

(11β,13α,17β)-11,17-Epoxy-9-fluoro-17-methyl-13-(phenylthio)-18-norandrosta-1,4-dien-3-one (A)

9-Fluoro-11β-hydroxy-17,17-bis(phenylthio)-androsta-1,4-dien-3-one

A solution of 13.5 g of 9-fluoro-11β-hydroxyandrosta1,4-diene-3,17-dione in 75 ml of dichloromethane and 75 ml of glacial acetic acid is stirred with 23 ml of thiophenol and 10 ml of boron trifluoride ethereate at room temperature under nitrogen. After 1.0 hour the solution is diluted with 350 ml of chloroform. The chloroform solution is washed successively with water, saturated sodium bicarbonate solution and water, dried over anhydrous sodium sulfate and evaporated in vacuo to give 17.6 g of an oil. This is dissolved in 1:3 hexane-chloroform and chromatographed on a 200 g-silica gel column. Elution with 1:3 hexanechloroform and chloroform gives impurities followed by 6.3 g of a tlc-homogeneous material. Crystallization from chloroform-methanol gives 5.0 g of the title compound, melting point 249°–250° C. (dec.).

(B)

9-Fluoro-11β-hydroxy-17-(phenylthio)androsta-1,4,16-trien-3-one

A suspension of 6.0 g of 9-fluoro-11β-hydroxy-17,17-bis(phenylthio)androsta-1,4-dien-3-one in 120 ml of diethylbenzene is stirred at 190° C. for 45 minutes. The solution is cooled at 0° C. and a solid crystallizes. This is filtered and dried in vacuo to give 5.5 g of material. Recrystallization from chloroform-methanol gives 4.21 g of the title compound, melting point 253°–255° C. (dec.).

(C)

(11β,13α,17β)-11,17-Epoxy-9-fluoro-17-methyl-13-(phenyl-thio)-18-norandrosta-1,4-dien-3-one 9-Fluoro-11β-hydroxy-17-(phenylthio)androsta-1,4,16-trien-3-one (3.0 g) is dissolved in 300 ml of very dry dichloromethane in a reaction vessel which is flammed and cooled under nitrogen. Then, 3.0 ml of boron trifluoride etherate is added and stirred for 3 hours at room temperature. The reaction mixture is quenched with 5% sodium bicarbonate and diluted with water. The phases are separated. The aqueous phase is extracted two more times with 100 ml of dichloromethane. The combined dichloromethane extracts are washed with water, dried with sodium sulfate and evaporated in vacuo. The residue is dissolved in chloroform and chromatographed on a silica gel column (60 g). The product from chromatography is crystallized from ethyl acetate and gives 2.45 g of the title compound as crystals melting at 212°–213° C. with decomposition.

EXAMPLE 3

(11β,13α,17β)-11,17-Epoxy-9-fluoro-17-methyl-13-(phenylsulfinyl)-18-norandrosta-1,4-dien-3-one (two isomers)

(11β,13α,17β)-11,17-Epoxy-9-fluoro-17-methyl-13-(phenylthio)-18-norandrosta-1,4-dien-3-one (1.23g, prepared as described in Example 2) is dissolved in 50 ml of dichloromethane. To this solution, 600 mg of meta-chloroperbenzoic acid is added and stirred at room temperature for 1 hour. Thin-layer chromatography shows spots of two isomeric sulfoxides and sulfone (trace only).

The reaction mixture is washed with 10% sodium bisulfite (50 ml), and 10% potassium carbonate. The aqueous phase is extracted with two 50 ml portions of dichloromethane. The combined extracts are washed with water, dried with sodium sulfate and evaporated in vacuo.

The two isomers are separated by thin-layer chromatography on 4 plates (2 mm thick, 20 × 20 cm of silica gel). The plates are developed three times with chloroform-ethyl acetate (7:3). The less polar isomer is crystallized from ethyl acetate to give 750 mg of product, melting point 185°–186° C., dec.

The more polar isomer is crystallized from ethyl acetate and gives 225 mg of product, melting point 171°–172° C., dec.

EXAMPLE 4

(11β,13α,17β)-11,17-Epoxy-9-fluoro-17-methyl-13-(phenylsulfonyl)-18-norandrosta-1,4-dien-3-one (11β,13α,17β)-11,17-Epoxy-9-fluoro-17-methyl-13-(phenylthio)-18-norandrosta-1,4-dien-3-one (820 mg., prepared as described in Example 2) is dissolved in 100 ml of dichloromethane and 820 mg of m-chloroperbenzoic acid (excess) is added and stirred at room temperature for 2 hours. The reaction mixture is washed with 100 ml of 10% sodium bisulfite, 100 ml of 10% potassium carbonate and water, dried with sodium sulfate and evaporated in vacuo. The residue is dissolved in chloroform and chromatographed on a column of silica gel (15 g). It gives 855 mg of pure material which is crystallized from ethyl acetate to give 780 mg of analytically pure product, melting point 226°–228° C. dec.

EXAMPLE 5

(11β,13α,17β)-11,17-Epoxy-13-(ethylthio)-9-fluoro-17-methyl-18-norandrosta-1,4-dien-3-one (A)

17,17-Bis(ethylthio)-9-fluoro-11β-hydroxyandrosta-1,4-dien-3-one

A solution of 9.5 g of 9-fluoro-11β-hydroxyandrosta-1,4-diene-3,17-dione in 50 ml of dichloromethane and 50 ml of glacial acetic acid is stirred with 11.2 g of ethanethiol and 7.5 ml of boron trifluoride etherate at room temperature under nitrogen. After 1.5 hours the solution is diluted with 350 ml of chloroform. The chloroform solution is washed with water, saturated sodium bicarbonate solution and water, dried over anhydrous sodium sulfate and evaporated in vacuo to give 11 g of a foam. This is dissolved in hexane-chloroform (2:1) and chromatographed on a 200 g-silica gel column. Elution with hexane-chloroform (2:1 and 1:1) gives 5.1 g of a tlc-homogeneous material. Crystallization from acetone-hexane gives 4.05 g of the title compound, melting point 276°–277° C., dec.

(B)

17-(Ethylthio)-9-fluoro-11β-hydroxyandrosta-1,4,16-trien-3-one

A suspension of 4.0 g of 17,17-bis(ethylthio)-9-fluoro-11β-hydroxyandrosta-1,4-dien-3-one (prepared as described above) in 60 ml of diethylbenzene is stirred at 190° C. (oil bath temperature) for 1 hour. The solution is cooled to 0° C. and the solid that precipitates is filtered. This is redissolved in 1:9 hexane-chloroform and chromatographed on a 60 g-silica gel column. Elution with 1:9 hexane-chloroform gives 3.35 g of a tlc-homogeneous material. Crystallization from chloroform-methanol gives 2.8 g of the title compound, melting point, 282°–283° C., dec.

(C)
(11β,13α,17β)-11,17-Epoxy-13-(ethylthio)-9-fluoro-17-methyl-18-norandrosta-1,4-dien-3-one To a suspension of 17-(ethylthio)-9-fluoro-11β-hydroxyandrosta-1,4,16-trien-3-one (2.8 g, prepared as described above) in 100 ml of dry dichloromethane under nitrogen is added 4.0 ml of boron trifluoride etherate at room temperature causing the solid to dissolve. After 1.0 hour the solution is added under stirring into an excess of dilute sodium bicarbonate solution. The dichloromethane layer is then separated, washed with water, dried, evaporated and the residue is chromatographed on a column of silica gel (80 g) using chloroform for elution to afford 1.67 g of the title compound. Crystallization of the 1.67 g of material from methanol affords the title compound (1.41 g), melting point 128°–130° C.

EXAMPLE 6

(11β,13α,17β)-11,17-Epoxy-13-(ethylsulfinyl)-9-fluoro-17-methyl-18-norandrosta-1,4-dien-3-one (two isomers)

A solution of (11β,13α,17β)-11,17-epoxy-13-(ethylthio)-9-fluoro-17-methyl-18-norandrosta-1,4-dien-3-one (677 mg, prepared as described in Example 5) in dichloromethane (25 ml) is stirred with m-chloroperbenzoic acid (85%, 400 mg) for 1 hour. Thin-layer chromatography shows that some of the starting material has not reacted and an additional 80 mg of m-chloroperbenzoic acid is added. After an additional 15 minutes, the solution is washed with a 10% sodium bisulfite solution, a 10% potassium carbonate solution and water, dried, evaporated and the residue subjected to preparative thin-layer chromatography on 2.0 mm silica gel plates (development with chloroform-ethyl acetate (3:1) to afford 655 mg of the title compound. This material is combined with 478 mg of material prepared in another run and crystallized twice from ethyl acetate-hexane to afford 540 mg of the title compound, melting point 193°–195° C., dec. This product is a mixture of sulfinyl stereoisomers.

EXAMPLE 7

(11β,13α,17β)-11,17-Epoxy-13-(ethylsulfonyl)-9-fluoro-17-methyl-18-androsta-1,4-dien-3-one A solution of (11β,13α,17β)-11,17-epoxy-13-(ethylsulfinyl)-9-fluoro-17-methyl-18-norandrosta-1,4-dien-3-one (696 mg) in dichloromethane (50 ml) is stirred with m-chloroperbenzoic acid (500 mg) for 1 hour. The solution is then washed successively with a 10% sodium bisulfite solution, a 10% sodium bicarbonate solution and water, dried, evaporated and the residue (760 mg) crystallized from methanol to yield 593 mg of the hydrate of the title compound, melting point 145°–147° C. A specimen crystallized from acetone-hexane has a melting point of 172°–174° C.

EXAMPLES 8–13

Following the procedure described in Example 1, but substituting the steroid listed in column I for 9-fluoro-11β-hydroxyandrosta-1,4-diene-3,17-dione and the compound listed in column II for methanethiol, yields the steroid product listed in column III.

|    | Column I | Column II | Column III |
|----|----------|-----------|------------|
| 8  | 11β-hydroxyandrosta-1,4-diene-3,17-dione | n-butanethiol | (11β,13α,17β)-13-(n-butylthio)-11,17-epoxy-17-methyl-18-norandrosta-1,4-dien-3-one |
| 9  | 9-iodo-11β-hydroxyandrosta-1,4-diene-3,17-dione | 1-mercapto-2-methylbenzene | (11β,13α,17β)-11,17-epoxy-9-iodo-17-methyl-13-[(2-methylphenyl)thio]-18-norandrosta-1,4-dien-3-one |
| 10 | 9-bromo-11β-hydroxyandrosta-1,4-diene-3,17-dione | 1-chloro-4-mercaptobenzene | (11β,13α,17β)-9-bromo-13-[(4-chlorophenyl)thio]-11,17-epoxy-17-methyl-18-norandrosta-1,4-dien-3-one |
| 11 | 6α,9-difluoro-11β-hydroxyandrosta-4-ene-3,17-dione | 1-mercapto-2-methoxybenzene | (11β,13α,17β)-11,17-epoxy-6α,9-difluoro-13-[(2-methyoxyphenyl)thio]-17-methyl-18-norandrost-4-ene-3-one |
| 12 | 9-chloro-11β-hydroxyandrosta-1,4-diene-3,17-dione | 1-mercapto-2,4-dimethylbenzene | (11β,13α,17β)-9-chloro-11,17-epoxy-17-methyl-13-[(2,4-dimethylphenyl)thio]-18-norandrosta-1,4-dien-3-one |
| 13 | 11β-hydroxy-6α-methylandrosta-1,4-diene-3,17-dione | methanethiol | (11β,13α,17β)-11,17-epoxy-6α,17-dimethyl-13-(n-methylthio)-18-norandrosta-1,4-dien-3-one |

EXAMPLES 14–19

Following the procedure of Example 6, but substituting the steroid listed in column I for (11β,13α,17β)-11,17-epoxy-13-(ethylthio)-9-fluoro-17-methyl-18-norandrosta-1,4-dien-3-one, yields the steroid product listed in column I as a mixture of sulfinyl stereoisomers.

|    | Column I | Column II |
|----|----------|-----------|
| 14 | (11β,13α,17β)-13-(n-butylthio)-11,17-epoxy-17-methyl-18-norandrosta-1,4-dien-3-one | (11β,13α,17β)-13-(n-butylsulfinyl)-11,17-epoxy-17-methyl-18-norandrosta-1,4-dien-3-one |
| 15 | (11β,13α,17β)-11,17-epoxy-9-iodo-17-methyl-13-[(2-methylphenyl)thio]-18-norandrosta-1,4-dien-3-one | (11β,13α,17β)-11,17-epoxy-9-iodo-17-methyl-13-[(2-methylphenyl)sulfinyl]-18-norandrosta-1,4-dien-3-one |
| 16 | (11β,13α,17β)-9-bromo-13-[(4-chlorophenyl)thio]-11,17-epoxy-17-methyl-18-norandrosta-1,4-dien-3-one | (11β,13α,17β)-9-bromo-13-[(4-chlorophenyl)sulfinyl]-11,17-epoxy-17-methyl-18-norandrosta-1,4-dien-3-one |
| 17 | (11β,13α,17β)-11,17-epoxy-6α,9-difluoro-13-[(2-methyoxyphenyl)thio]-17-methyl-18-norandrosta-4-ene-3-one | (11β,13α,17β)-11,17-epoxy-6α,9-difluoro-13-[(2-methoxyphenyl)sulfinyl]-17-methyl-18-norandrosta-4-ene-3-one |
| 18 | (11β,13α,17β)-9-chloro-11,17-epoxy-17-methyl-13-[(2,4-dimethylphenyl)thio]-18-norandrosta-1,4-dien-3-one | (11β,13α,17β)-9-chloro-11,17-epoxy-17-methyl-13-[(2,4-dimethylphenyl)sulfinyl]-18-norandrosta-1,4-dien-3-one |
| 19 | (11β,13α,17β)-11,17-epxoy-6α,17-dimethyl-13- | (11β,13α,17β)-11,17-epoxy-6α,17-dimethyl-13-(n-methyl- |

| Column I | Column II |
|---|---|
| n-(methylthio)-18-norandrosta-1,4-dien-3-one | sulfinyl)-18-norandrosta-1,4-dien-3-one |

EXAMPLES 20-25

Following the procedure of Example 7, but substituting the steroid listed in column I for (11β,13α,17β)-11,17-epoxy-13-(ethylsulfinyl)-9-fluoro-17-methyl-18-norandrosta-1,4-dien-3-one, yields the steroid product listed in column II.

| | Column I | Column II |
|---|---|---|
| 20 | (11β,13α,17β)-13-(n-butylsulfinyl)-11,17-epoxy-17-methyl-18-norandrosta-1,4-dien-3-one | (11β,13α,17β)-13-(n-butylsulfonyl)-11,17-epoxy-17-methyl-18-norandrosta-1,4-dien-3-one |
| 21 | (11β,13α,17β)-11,17-epoxy-9-iodo-17-methyl-13-[(2-methylphenyl)sulfinyl]-18-norandrosta-1,4-dien-3-one | (11β,13α,17β)-11,17-epoxy-9-iodo-17-methyl-13-[(2-methylphenyl)sulfonyl]-18-norandrosta-1,4-dien-3-one |
| 22 | (11β,13α,17β)-9-bromo-13-[(4-chlorophenyl)sulfinyl]-11,17-epoxy-17-methyl-18-norandrosta-1,4-dien-3-one | (11β,13α,17β)-9-bromo-13-[(4-chlorophenyl)sulfonyl]-11,17-epoxy-17-methyl-18-norandrosta-1,4-dien-3-one |
| 23 | (11β,13α,17β)-11,17-epoxy-6α,9-difluoro-13-[(2-methoxyphenyl)sulfinyl]-17-methyl-18-norandrosta-4-ene-3-one | (11β,13α,17β)-11,17-epoxy-6α,9-difluoro-13-[(2-methoxyphenyl)sulfonyl]-17-methyl-18-norandrosta-4-ene-3-one |
| 24 | (11β,13α,17β)-9-chloro-11,17-epoxy-17-methyl-13-[(2,4-dimethylphenyl)sulfinyl]-18-norandrosta-1,4-dien-3-one | (11β,13α,17β)-9-chloro-11,17-epoxy-17-methyl-13-[(2,4-dimethylphenyl)sulfonyl]-18-norandrosta-1,4-dien-3-one |
| 25 | (11β,13α,17β)-11,17-epoxy-6α,17-dimethyl-13-(n-methylsulfinyl)-18-norandrosta-1,4-dien-3-one | (11β,13α,17β)-11,17-epoxy-6α,17-dimethyl-13-(n-methylsulfonyl)-18-norandrosta-1,4-dien-3-one |

What is claimed is:

1. A steroid having the formula

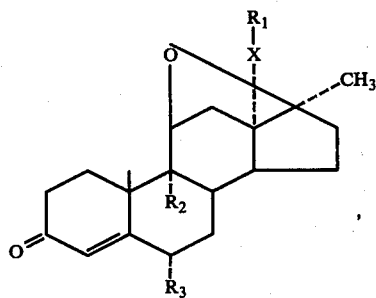

or the 1,2-dehydro derivative thereof, wherein X is —S—,

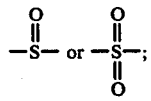

$R_1$ is alkyl, phenyl or phenyl substituted with one or two alkyl, alkoxy or halogen substituents; $R_2$ is hydrogen or halogen; $R_3$ is hydrogen, fluorine or methyl; and wherein the terms "alkyl" and "alkoxy" refer to groups having 1 to 10 carbon atoms.

2. A steroid in accordance with claim 1 wherein X is —S—.

3. A steroid in accordance with claim 1 wherein X is

4. A steroid in accordance with claim 1 wherein X is

5. A steroid in accordance with claim 1 wherein $R_3$ is hydrogen.

6. A steroid in accordance with claim 1 wherein $R_2$ is fluorine.

7. A steroid in accordance with claim 5 wherein $R_2$ is fluorine.

8. A steroid in accordance with claim 1 wherein $R_1$ is alkyl.

9. A steroid in accordance with claim 1 wherein $R_1$ is phenyl or phenyl substituted with one or two alkyl, alkoxy or halogen substituents.

10. A steroid in accordance with claim 9 wherein $R_1$ is phenyl.

11. The steroid in accordance with claim 1, (11β,13α,17β)-11,17-epoxy-9-fluoro-17-methyl-13-(methyl-thio)-18-norandrosta-1,4-dien-3-one.

12. The steroid in accordance with claim 1, (11β,13α,17β)-11,17-epoxy-9-fluoro-17-methyl-13-(phenylthio)-18-norandrosta-1,4-dien-3-one.

13. The steroid in accordance with claim 1, (11β,13α,17β)-11,17-epoxy-9-fluoro-17-methyl-13-(phenyl-sulfinyl)-18-norandrosta-1,4-dien-3-one (two isomers).

14. The steroid in accordance with claim 1, (11β,13α,17β)-11,17-epoxy-9-fluoro-17-methyl-13-(phenyl-sulfonyl)-18-norandrosta-1,4-dien-3-one.

15. The steroid in accordance with claim 1, (11β,13α,17β)-11,17-epoxy-13-(ethylthio)-9-fluoro-17-methyl-18-norandrosta-1,4-dien-3-one.

16. The steroid in accordance with claim 1, (11β,13α,17β)-11,17-epoxy-13-(ethylsulfinyl)-9-fluoro-17-methyl-18-norandrosta-1,4-dien-3-one.

17. The steroid in accordance with claim 1, (11β,13α,17β)-11,17-epoxy-13-(ethylsulfonyl)-9-fluoro-17-methyl-18-androsta-1,4-dien-3-one.

* * * * *

UNITED STATES PATENT AND TRADEMARK OFFICE
CERTIFICATE OF CORRECTION

PATENT NO. : 4,133,811
DATED : January 9, 1979
INVENTOR(S) : Ravi K. Varma

It is certified that error appears in the above-identified patent and that said Letters Patent are hereby corrected as shown below:

Col. 2, line 15, "IV 1. $R_1$-SH" should read -- IV  $R_1$-SH --.

Col. 4, lines 14 and 15, "androstal,4-" should read

-- androsta-1,4- --.

Signed and Sealed this

Twenty-fourth Day of April 1979

[SEAL]

Attest:

RUTH C. MASON
Attesting Officer

DONALD W. BANNER
Commissioner of Patents and Trademarks